United States Patent
Tynan, Jr. et al.

(10) Patent No.: US 9,689,791 B2
(45) Date of Patent: Jun. 27, 2017

(54) TESTING DEVICE AND METHODS FOR TESTING TAPE SEAL STRENGTH

(71) Applicant: Intertape Polymer Corp., Sarasota, FL (US)

(72) Inventors: John K. Tynan, Jr., Marysville, MI (US); Kenneth Joseph Zanon, II, Sparta, WI (US); Nicholas John Carter, Grosse Pointe, MI (US)

(73) Assignee: INTERTAPE POLYMER CORP., Sarasota, FL (US)

( * ) Notice: Subject to any disclaimer, the term of this patent is extended or adjusted under 35 U.S.C. 154(b) by 154 days.

(21) Appl. No.: 14/723,025

(22) Filed: May 27, 2015

(65) Prior Publication Data
US 2015/0346079 A1 Dec. 3, 2015

Related U.S. Application Data

(60) Provisional application No. 62/003,122, filed on May 27, 2014.

(51) Int. Cl.
*G01N 19/04* (2006.01)
(52) U.S. Cl.
CPC .................... *G01N 19/04* (2013.01)
(58) Field of Classification Search
CPC ..................................................... G01N 19/04
See application file for complete search history.

(56) References Cited

U.S. PATENT DOCUMENTS

| | | | | |
|---|---|---|---|---|
| 2,361,751 A | * | 10/1944 | Donovan | D21J 1/16 156/276 |
| 2,453,338 A | * | 11/1948 | Pajak | G01B 13/06 33/833 |
| 2,694,924 A | * | 11/1954 | Matlock | G01M 3/2869 73/159 |
| 2,799,156 A | * | 7/1957 | Southwick, Jr. | G01N 19/04 73/150 R |
| 2,982,129 A | * | 5/1961 | Wetzel | G01N 19/04 73/150 R |
| 3,396,578 A | * | 8/1968 | Skundberg | G01N 19/04 73/150 A |
| 4,043,179 A | * | 8/1977 | Ingle, Jr. | G01N 19/04 73/37 |
| 4,393,699 A | * | 7/1983 | Seiler, Jr. | G01N 19/04 73/150 A |

(Continued)

OTHER PUBLICATIONS

PCT, International Search Report and Written Opinion; Application No. PCT/US2015/032553 (Aug. 26, 2015).

*Primary Examiner* — David Bolduc
(74) *Attorney, Agent, or Firm* — Thompson Hine LLP

(57) ABSTRACT

A testing device for testing adhesion seal strength of a tape to a substrate. The testing device includes a body defining a chamber having a first port in fluid communication with the chamber, a platform sealingly attached to the chamber and having an elongate opening or a plurality of openings therethrough as a second port of the chamber. The testing device further includes a frame removably mounted to the platform. The frame defines a perimeter that surrounds the second port and, when mounted to the platform, secures a test substrate thereunder against the platform with a fluid-tight seal. Methods for preparing a test sample and methods of operating the testing device are also disclosed.

20 Claims, 7 Drawing Sheets

(56) References Cited

U.S. PATENT DOCUMENTS

| | | | |
|---|---|---|---|
| 4,586,371 A | | 5/1986 | Ivie et al. |
| 4,740,424 A | * | 4/1988 | Schumacher ........ C09D 175/04 |
| | | | 427/208.4 |
| 4,768,376 A | | 9/1988 | Lanham, Jr. et al. |
| 4,911,964 A | * | 3/1990 | Corbo .................... E06B 3/285 |
| | | | 428/212 |
| 5,127,260 A | * | 7/1992 | Robertson ............... G01M 3/36 |
| | | | 73/150 A |
| 5,261,268 A | | 11/1993 | Namba |
| 5,542,288 A | | 8/1996 | Fenlon |
| 5,575,868 A | | 11/1996 | Mann |
| 5,616,852 A | * | 4/1997 | Tsubota .................. G01L 5/105 |
| | | | 73/159 |
| 6,450,041 B1 | | 9/2002 | Ali |
| 2004/0149026 A1 | * | 8/2004 | Potyrailo ............... G01N 33/32 |
| | | | 73/150 R |
| 2008/0289279 A1 | * | 11/2008 | Hannan ................ E04B 1/7069 |
| | | | 52/506.05 |
| 2013/0213127 A1 | * | 8/2013 | Tynan, Jr. .............. G01N 19/04 |
| | | | 73/150 A |

* cited by examiner

TESTING DEVICE AND METHODS FOR TESTING TAPE SEAL STRENGTH

RELATED APPLICATIONS

This application claims the benefits of U.S. Provisional Application No. 62/003,122, filed on May 27, 2014, which is incorporated by reference herein in its entirety.

TECHNICAL FIELD

The present disclosure relates generally to devices and methods for testing the seal strength of tapes to substrates, and more particularly to devices and methods for testing the seal strength of sheathing tape to sheathing products for architectural structures, e.g., house wrap.

BACKGROUND

Sheathing tape is widely used in the construction industry to secure sheets of house wrap together, to seal joints in foam insulation, to repair tears and rips in construction materials that include vapor barriers, to improve the energy efficiency of the structure and for other similar purposes. If sheathing tape fails, for example along a seam of house wrap on an exterior wall of a house or other structure, water and air may penetrate through the barrier formed by the house wrap and reach the wall, creating a significant risk of damage from mold, wood rot, and other moisture-related problems as well as a loss of energy.

Given the variety of house wraps and other construction materials which may serve as a substrate for sheathing tape, each with its own unique physical characteristics, the performance (i.e. adhesion strength) of a given sheathing tape may vary depending upon the particular substrate to which the sheathing tape is adhered. To that end, it is desirable to have a device and method for testing a seal strength of various tape-substrate combinations in a controlled setting.

SUMMARY

In one aspect of the present disclosure, a testing device for testing adhesion seal strength of a tape to a substrate includes a body defining a chamber having a first port in fluid communication with the chamber; a platform sealingly attached to the chamber and having an elongate opening or a plurality of openings therethrough as a second port of the chamber; and a frame removably mounted to the platform. The frame defines a perimeter surrounding the second port and, when the frame is mounted to the platform, the frame secures a test substrate thereunder against the platform with a fluid-tight seal.

In another aspect of the previous embodiment, the testing device includes a regulator coupled to the first port for introduction of a gas into the chamber. In another aspect, the testing device includes one or more fasteners removably mounting the frame to the platform. In another embodiment, the testing device includes a pressure gauge in fluid communication with the chamber. In another embodiment, the testing device includes a gas-flow meter in fluid communication with the chamber.

In another aspect of the previous embodiments, the platform includes a seal positioned to create the fluid-tight seal with the test substrate when the frame is mounted to the platform. In another aspect, the body defining the chamber is below the platform opposite the frame, and the first port acts as an inlet for fluid. In another aspect, the body defining the chamber is mounted to an upper surface of the frame opposite a lower surface thereof, which is seated on the platform, and the first port acts as an outlet for fluid. In another aspect of the previous embodiment, the testing device includes a second body sealingly mounted to an upper surface of the frame opposite a lower surface thereof, which is seated on the platform thereby defining an upper chamber; wherein the upper chamber includes a third port. In another aspect of the previous few embodiments, the chamber and/or the upper chamber includes a pressure sensor.

In another aspect of the disclosure, a method for testing the adhesion seal strength of tape to a substrate includes providing a tape testing device that includes: a body defining a chamber having a first port in fluid communication with the chamber; a platform sealingly attached to the chamber and having an elongate opening or a plurality of openings therethrough defining a second port of the chamber; and a frame removably mounted to the platform, wherein the frame defines a perimeter surrounding the second port and, when the frame is mounted to the platform, the frame secures a test substrate thereunder against the platform with a fluid-tight seal. The method further includes: providing a test substrate having an opening therethrough that generally matches the elongate opening or plurality of openings in the platform and a length of adhesive tape adhered thereto in a position that covers the elongate opening or plurality of openings therein to define a test seal; securing the test substrate between the frame and the platform of the tape testing device; allowing a fluid to flow into or out of the chamber of the testing device using the first port thereof; and monitoring the test seal.

In another aspect of the previous embodiment, the method further includes applying a failure detecting agent to the test substrate along an edge of the length of adhesive tape. The failure detecting agent can include one or more of a dye, a detergent, a piece of material, or a plurality of pieces of material. In another embodiment, allowing a fluid to flow into the chamber includes selecting a target pressure and adding fluid until the target pressure is achieved. In another embodiment, allowing a fluid to flow into the chamber includes selecting a first target pressure and a second target pressure, and adding fluid until the first target pressure is achieved, and thereafter incrementally increasing a flow of fluid into the chamber until the second target pressure is achieved. In another embodiment, allowing a fluid to flow into the chamber includes gradually, continually increasing the flow of fluid into the chamber until a failure of the test seal occurs and recording a pressure value.

In another aspect of the previous embodiments of the method, monitoring the test seal includes visual observation by a user of one or more failure points detectable as a bubble between the test substrate and the length of adhesive tape or a leak of fluid from the chamber. In another aspect of the disclosed method, the test substrate is house wrap and the adhesive tape is sheathing tape. In another aspect of the disclosed method, the method further includes maintaining, at the target pressure, a constant flow of fluid for a selected interval of time.

The above and other features of the invention, its nature and various advantages will be more apparent upon consideration of the following detailed description, taken in conjunction with the accompanying drawings.

DETAILED DESCRIPTION

Figure 1:
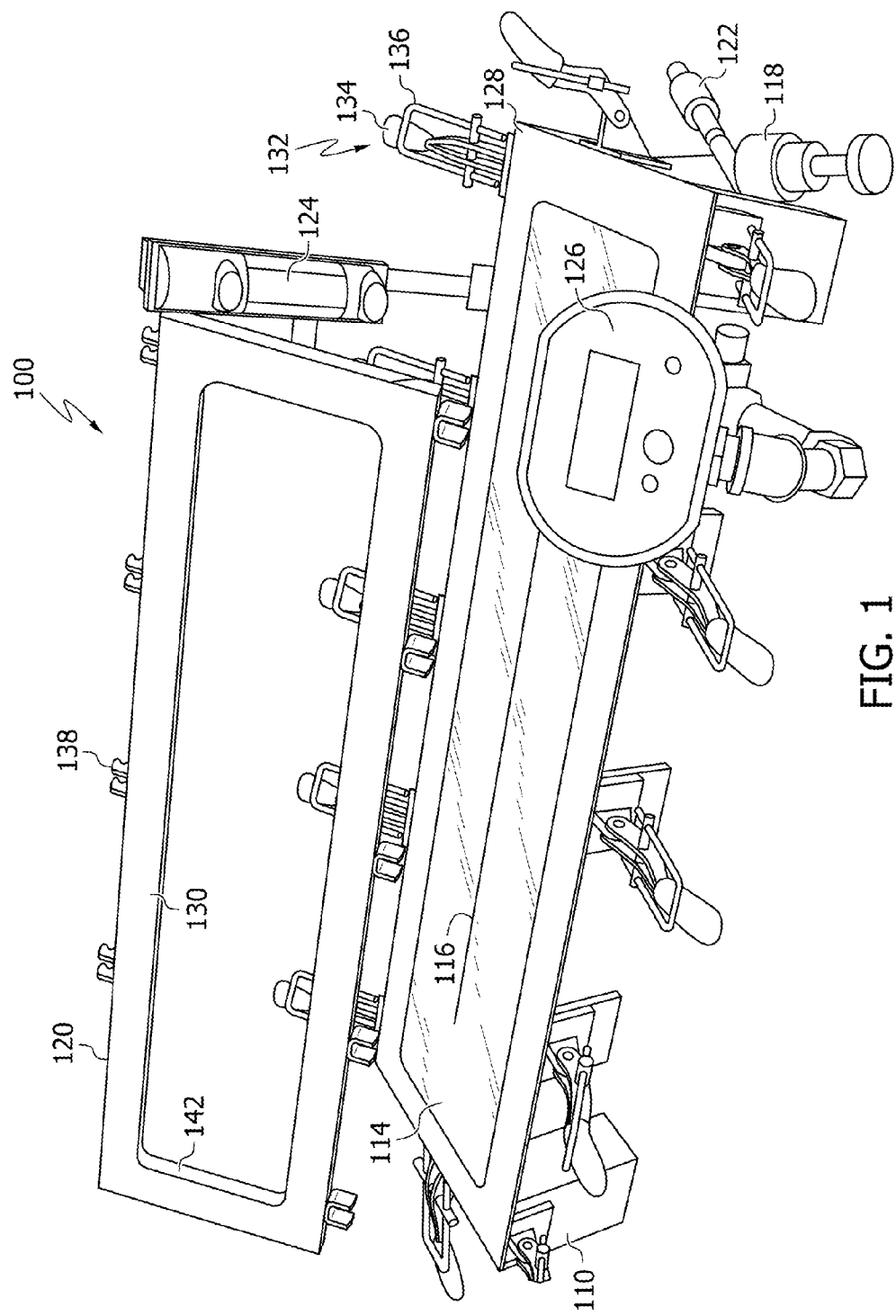
FIG. 1 is a front perspective view of a testing device disclosed herein, in an open position.

The following detailed description will illustrate the general principles of the invention, examples of which are additionally illustrated in the accompanying drawings. In the drawings, like reference numbers indicate identical or functionally similar elements.

As used herein "fluid" means any liquid, suspension, colloid, gas, plasma, or combinations thereof.

Figure 2:
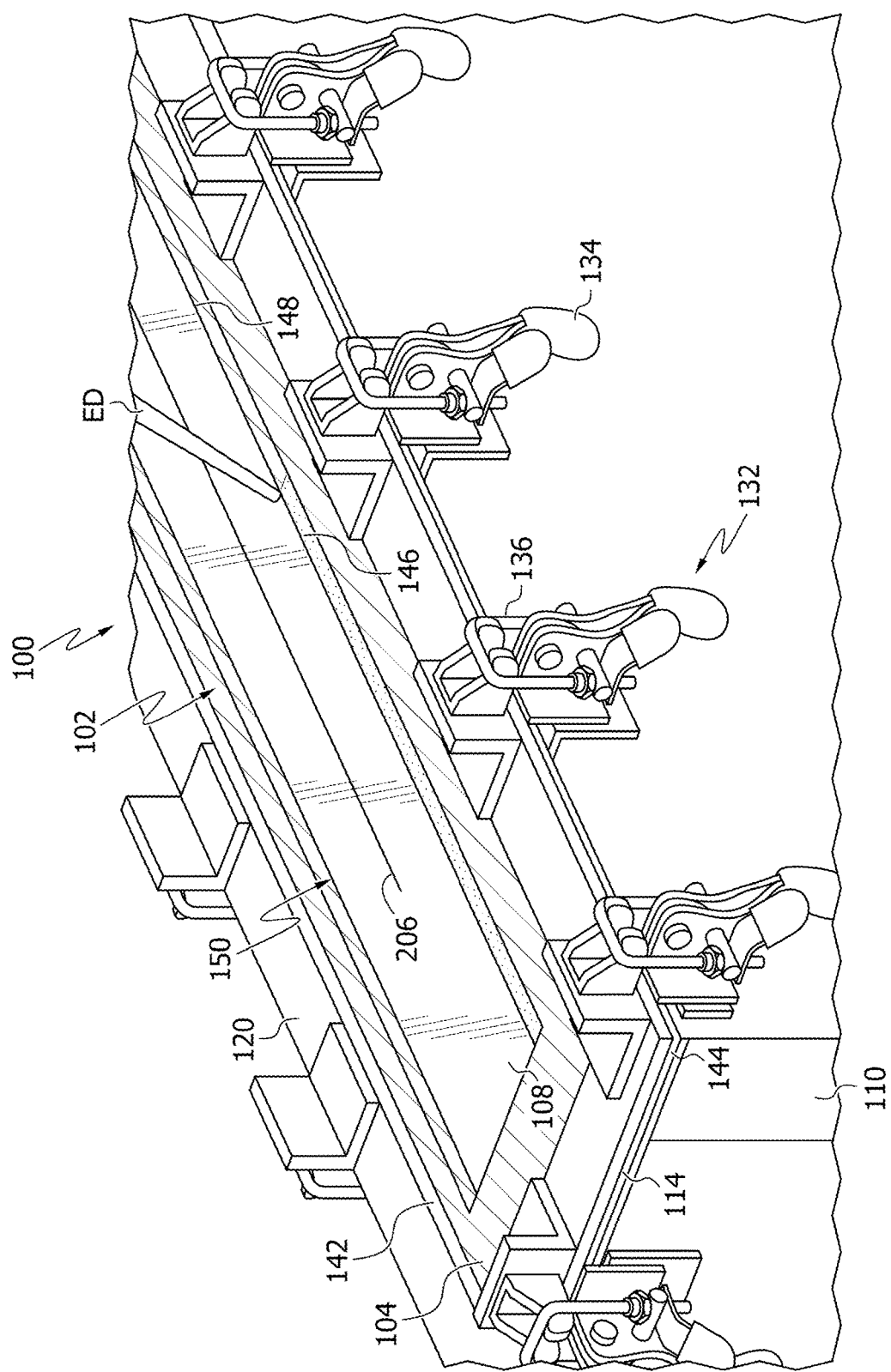
FIG. 2 is a partial perspective view of the testing device of FIG. 1 in a closed position.
Figure 3:
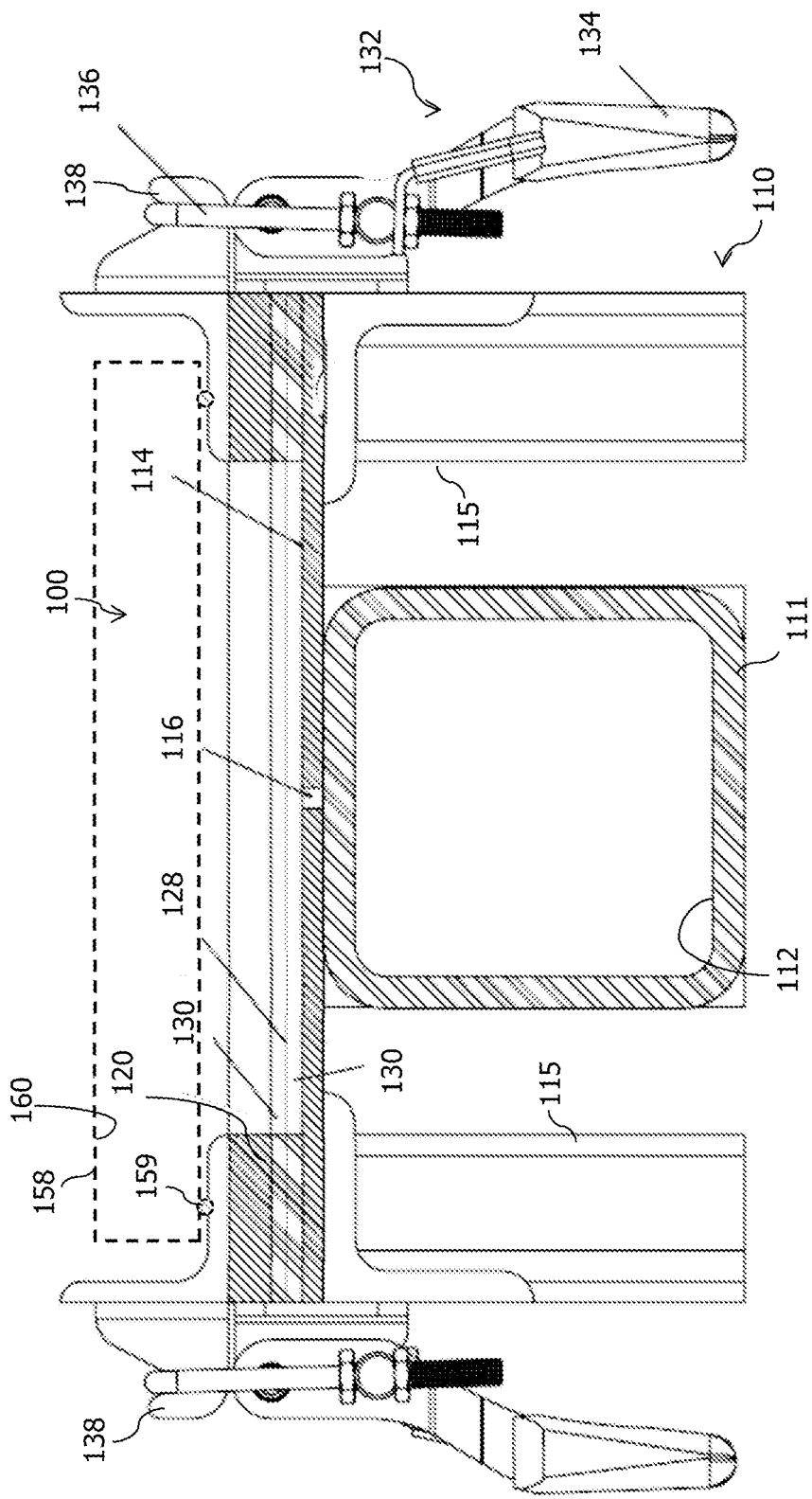
FIG. 3 is a cross-sectional view transverse to the longitudinal axis of the testing device of FIG. 1

Referring to FIGS. 1-3, a testing device 100 for testing a test sample 102 (FIG. 2) includes a base 110 having the following: a body 111, which defines chamber 112; a platform 114; a plurality of legs 115; and a plurality of releasable fasteners 132. The testing device 100 also includes a frame 120 (or lid) releasably mountable to the platform 114 of the base 110, by way of the plurality of releasable fasteners 132, to secure the test sample 102 against the platform 114. The legs 115 support the base 110 and may be coupled to the underside of the platform 114, to the body 111, or to another part of the base 110. The base 110 may also have a housing (not shown) enclosing the base 110. In FIG. 1 the testing device 100 is in an open position, set to receive a test sample.

Referring again to FIGS. 1 and 3, the body 111 is positioned generally beneath the platform 114, and an interface between the body 111 and the platform 114 is sealed to prevent fluids under pressure from penetrating between the body 111 and the platform 114 and escaping from the chamber 112. The chamber 112, which is defined within an interior of the body 111, includes an inlet 118 (or an outlet 118 depending on how the test device is operated) in fluid communication therewith. The inlet 118 allows a fluid, such as air, to pass through the inlet 118 and into the chamber 112. The testing device may further include a variety of monitoring and/or control devices, as shown in FIG. 1, in fluid communication with the chamber 112. These monitoring/control devices may include, but are not limited to: a regulator 122 that may be used to control fluid flow through the inlet 118; a meter 124 that may be used to monitor fluid flow or measure a quantity of fluid introduced to the chamber 112; a pressure gauge 126 to monitor and/or record the fluid pressure within the chamber 112; and a timer (not shown). The monitoring/control devices may be removably or non-removably coupled to the base 110. The chamber 112 may have any number of inlets and outlets, in addition to inlet 118 and opening 116 in the platform 114, to accommodate components such as the regulator 122, the meter 124, the pressure gauge 126, and/or other features in fluid communication with the chamber 112. However, each inlet and outlet, other than the inlet 118 and the opening 116, is closable, sealable, or otherwise configurable such that the chamber 112 and all associated components establish a closed, fluid-tight system (except for the inlet 118 and the opening 116), thereby defining a fluid flow path from the inlet 118, into the chamber 112, and out through opening 116 in the platform 114.

Referring to FIG. 1, the platform 114 is a generally flat surface, and may be positioned on the top side of the base 110. The platform 114 may also be positioned along any of the sides of the base 110. The platform 114 may include a seal or gasket 128 generally positioned along a perimeter of the platform 114. When the testing device 100 is in the closed position, the test sample 102 is positioned between the platform 114 and the frame 120 and a perimeter of the test sample 102 is compressed between the seal 128 and the frame 120 such that the seal 128 defines a primary sealing surface between the platform 114 and the test sample 102. When the testing device 100 is in the closed position, the seal 128 creates a fluid-tight seal 144 between the platform 114 and the test sample 102. The seal 128 may be monolithic with the platform 114 and/or the base 110, or the seal 128 may be attached thereto. The frame 120 may also include a supplemental seal or gasket 130 positioned about a perimeter of the frame 120. The supplemental seal 130 may create a fluid-tight seal with a side of the test sample 102 facing away from the platform 114 when the testing device 100 is in the closed position. The platform 114 (and corresponding frame 120) may be generally rectangular in shape or may have any other convenient shape, such as square, round, elliptical, polygonal, or other shape, for example, so long as the test sample 102 may be secured within the testing device 100. When the testing device 100 is closed, an outer perimeter of the platform 114 may or may not generally conform with an outer perimeter of the frame 120. For example, the outer perimeter of the platform 114 may extend further in one or all directions from the outer perimeter of the frame 120 without impacting the functionality of the testing device 100.

Still referring to FIG. 1, the platform 116 has an opening 116 that extends through the platform 114 and forms a second opening of the chamber 112. Opening 116 is positioned within the area of the platform 114 entirely bounded by the seal 128. As seen in FIGS. 1 and 3, the opening 116 defines an outlet for the chamber 112, such that pressurized fluid, for example air, introduced into the chamber 112 via the inlet 118 may escape or flow out of the chamber 112 via the opening 116. The opening 116 may be an elongate opening, for example a narrow slit, that extends across a substantial portion of the length of the platform 114, for example at least about 25%, at least about 50%, or at least about 75% of the length of the platform. A length of the opening 116 may depend upon the length of the platform and may be any length less than the length of the platform, but should not extend to or under the seal 128. In some embodiments, the opening 116 is about 12 inches long and is centrally located on the platform 114, which has a length of about 18 inches and a width of about 6 inches. Depending upon the size of the platform 114, the opening 116 may be shorter or longer. The opening 116 need not be centered in the platform 114, but to ensure proper sealing, the opening 116 should not extend to or under the seal 128 (FIG. 1). The opening 116 may have a width that is substantially less than the length of the opening 116. The width of the opening 116 may be from about 1/64 to about 1/2 inch (0.08 cm to 1.27 cm). In some embodiments, the width of the opening 116 may be greater than 1/2 inch (1.27 cm). In some embodiments, the width of the opening 116 may be about 1/8 inch (0.32 cm). The base 110 and chamber 112 may take any of a variety of shapes or forms to define the platform 114 and the opening 116 described above.

Figure 8:
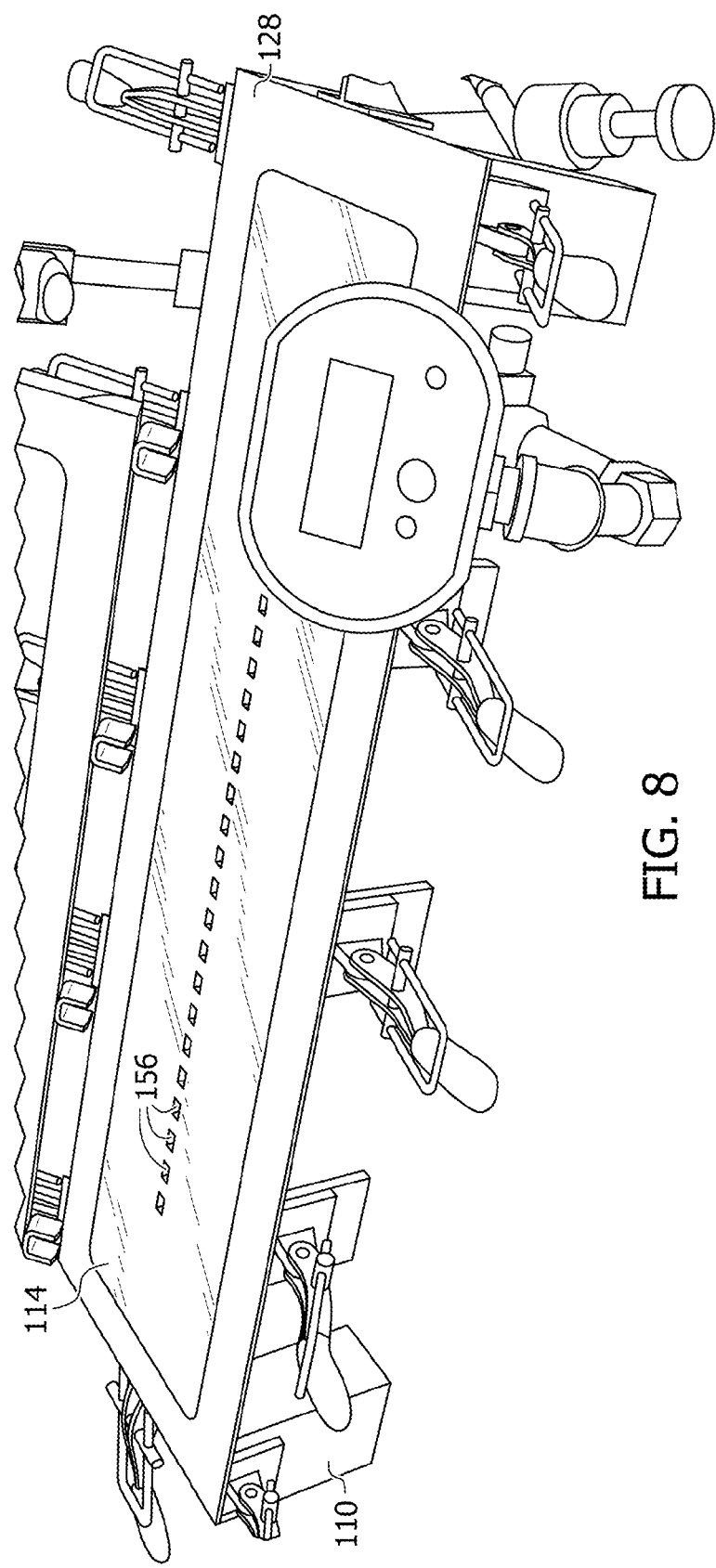
FIG. 8 is a front perspective view of an alternative embodiment of the testing device of FIG. 1 having a plurality of openings defining the outlet of the chamber.

The opening 116 is shown in FIG. 1 as an elongate opening, but is not limited thereto. As seen in FIG. 8, the "opening 116" may be a plurality of openings 156 arranged in a generally straight line or may be a plurality of openings arranged in a selected pattern (not shown). The plurality of openings 156 may be a plurality of slots or holes.

Referring back to FIGS. 1-3, the frame 120 of the testing device 100 is removably mounted to the platform 114 and configured for securing the test substrate 104 (FIG. 2) therebetween over the opening 116 to establish a fluid-tight/air-tight seal 144 between the test sample 102 and the platform 114 of the housing 110. The frame 120 defines a window 142 in a central portion of the frame 120. The window 142 provides a view of the test sample 102 during the testing process. The window 142 may be open or empty and may have a shape and size that is less than a size and shape of the platform 114 so that the window 142 does not interfere with creating a seal between the test sample 102 and the platform 114. The window 142 may also have a transparent shield or cover (not shown). The frame 120 is clamped to the platform 114 with the test sample 102 disposed or sandwiched therebetween. The frame 120 thereby applies pressure to the test sample 102 to form a fluid-tight seal against the platform 114, in particular against the seal 128 of the base as earlier described, while simultaneously providing an unobstructed view of the test sample 102 through the window 142. This facilitates visual observation of the test sample 102 during a test. As previously noted, the frame 120 may also include a supplemental seal 130 positioned around the perimeter of the frame 120 on a side of the frame 120 facing towards the platform 114. The supplemental seal 130 may facilitate creating a fluid-tight seal between the testing device 100 and the test sample 102.

Referring to FIGS. 1-2, the testing device 100 includes one or more releasable fasteners 132 that secure the frame 120 to the platform 114 when the testing device is in the closed position. The fasteners 132 apply pressure to the frame 120 seated against the platform 114 to reinforce and/or establish the fluid-tight/air-tight seal between the platform 114 and the test sample 102. In the depicted embodiment, the fasteners are clamps, but the fasteners 132 may take any other convenient form, including but not limited to screw features, ties, magnetic closures, and the like. The fasteners 132 may be positioned on the frame 120, the platform 114, other portions of the base 110, or a combination thereof. The fasteners 132 may be securely coupled to the base 110 or to one or more brackets coupled to the base 110. The fastener 132 may include a clamp having a handle 134 and a latch 136 attached to the base 110, and a receiving portion 138 attached to the frame 120. The receiving portion 138 may have a shape configured to receive the latch 136, such as a hooked shape. To secure the testing device 100 in the closed position, each latch 136 is received in an associated receiving portion 138, and the corresponding handle 134 is lowered to a locked position to fix the latch 136 within the hooked receiving portion 138.

Referring now to FIG. 2, the testing device 100 is shown in a closed position with a test sample 102 secured therein. The test sample 102 includes a test substrate 104 having a shape generally conforming to the shape of the platform and a slit 206 therein, and a strip of adhesive tape 108 adhered to the test substrate 104 to cover the slit 206, thereby sealing the slit 206 and forming a test seal 150. In operation, the testing device 100 receives the test sample 102 therein, as shown in FIG. 2. The test sample 102 may be positioned with a substrate 104 side facing towards the platform 114 and the strip of adhesive tape 108 facing outward away from the platform 114. In some embodiments, the test sample 102 may be positioned with the strip of adhesive tape 108 generally over-lapping the opening 116 in the platform 114. A fluid-tight seal is established for the test sample 102 against the platform 114 (FIG. 1) by the application of pressure thereto by the frame 120 and fasteners 132. A flow of fluid into the testing device 100 is used to apply fluid pressure against the test sample 102 along the slit 206 of the test substrate 104 (on a side thereof opposite the strip of adhesive tape 108), thereby testing the seal strength of the test seal 150 between the adhesive tape 108 and the test substrate 104. Seal strength refers to the test seal's 150 ability to withstand the applied force/pressure of the fluid and prevent leakage of the fluid between the tape 108 and the substrate 104.

Though the fluid flowing into the testing device 100 and into the chamber 112 may freely escape the chamber 112 via the opening 116 of the platform 114, the fluid-tight seal 144 between the test sample 102 and the platform 114 prevents the flow of fluid beyond a space defined and bounded by the platform 114 and the bottom surface of the test sample 102. Thus, so long as the test seal 150 holds, the test sample 102 prevents the egress of the fluid from the chamber 112. Consequently, as fluid flows into the system through the inlet 118 of the chamber 112, pressure builds up within the chamber 112, which can be monitored, for example with the pressure gauge 126. The pressure from the amount of fluid within chamber 112 applies a force to the underside of the test sample 102, thereby stressing the test seal 150 along the opening 106 of the test substrate 104. By design, the test seal 150 is weaker than the fluid-tight/air-tight seal 144 so that adhesive failures between the adhesive tape 108 and the test substrate 104 can be observed and quantified.

The testing device 100 may be used to test a variety of adhesive tapes in combination with a variety of test substrates, thereby facilitating repeatable, "apples-to-apples" comparison for seal strength across a variety of tape-substrate combinations. The testing device, adhesive tapes and substrates can be tested in a variety of environments, i.e., combinations of temperature, humidity and Ultraviolet light exposure.

In preparation for testing a test sample 102 using the testing device 100, the test sample 102 must be prepared. Referring to FIG. 2, the test sample 102 includes a test substrate 104 and an adhesive tape 108 selected for testing. The test substrate 104 may be any sheet-like material, for example house wrap, paper, plastic, metal foil, wood, polymer, or other suitable material. The adhesive tape 108 may be any adhesive tape, including sheathing tape, duct tape, masking tape, electrical tape, or any other adhesive tape, pressure-sensitive or otherwise, which is to be adhered to the test substrate 104 to establish the test seal 150 of the test sample 102. To avoid complications in testing, the test substrate 104 and adhesive tape 108 should be selected such that unbroken sections of the substrate 104 and tape 108 are each capable of containing and resisting the fluid force to be applied during the test. For example, the test substrate 104 and tape 108 should not contain holes or other infirmities that would readily facilitate the transmission of pressurized fluid therethrough.

Figure 4:
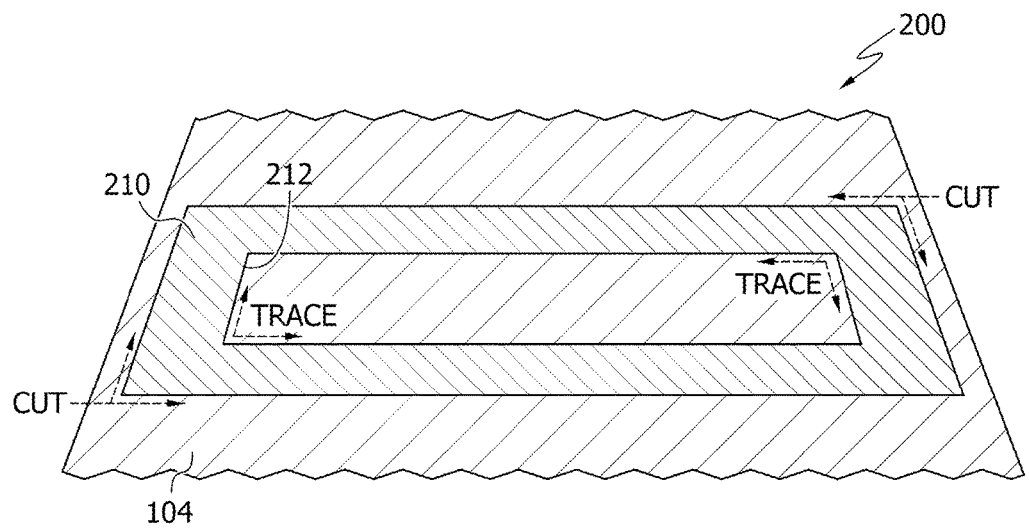
FIGS. 4-7 are perspective views illustrating portions of a process for preparing a test piece for use with the testing device of FIG. 1.
Figure 5:
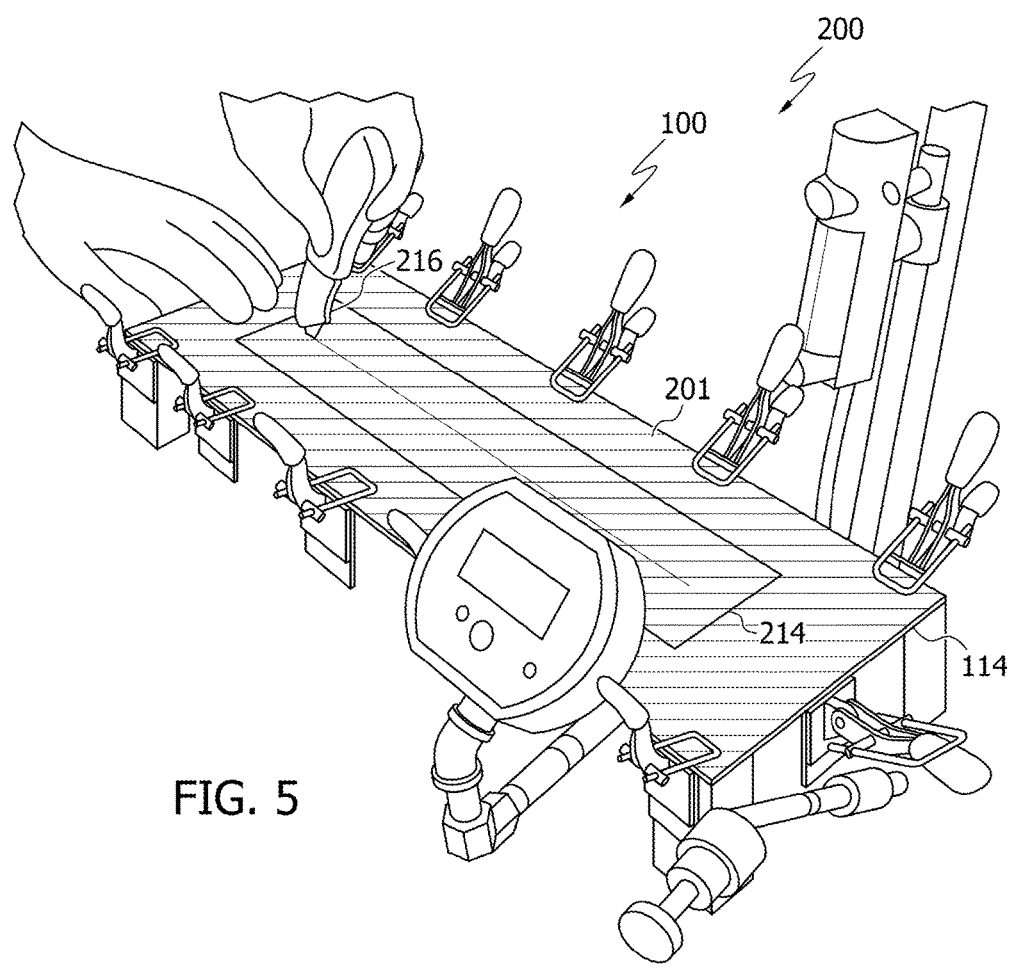
Figure 6:
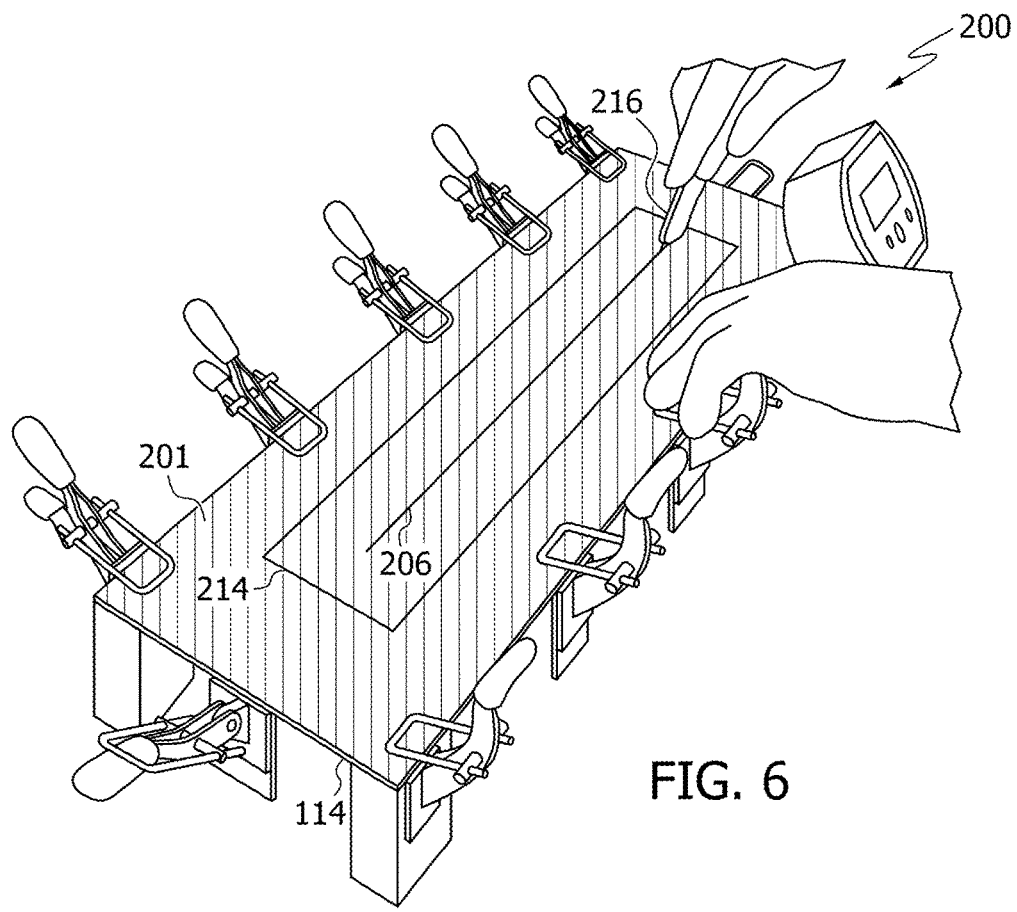

Referring now to FIGS. 4-6, a process 200 for preparing the test sample is as follows: select a test substrate 104; reduce the test substrate 104 to a test piece 201 of appropriate size to fit the platform 114 of the testing device 100, which may include providing a template 210 for cutting the test piece 201 from the test substrate, as shown in FIG. 4; place the test piece 201 on the platform 114, holding or clamping to the platform without the frame 120 that is shown in FIG. 1; and cut the test piece 201 by inserting a blade 216 into the opening 116 (FIG. 1) in the platform, as shown in FIG. 5, and moving the blade the length of the opening 116, as shown in FIG. 6, to form a slit 206 in the test piece 201. In process 200, the slit 206 may be generally similar in size and shape to the opening 116 of the platform 114 such that it conforms to the size and shape of the opening 116. If the opening 116 is a plurality of openings or holes, as shown in FIG. 8, this step may be repeated as many times as necessary and modified as necessary to have the openings in the test piece match the plurality of openings or holes or have a shape that aligns with the plurality of openings once the test piece is secured to the platform 114 by the frame 120. In one embodiment, a die may be provided that matches the configuration of the plurality of openings or holes in the platform 114 and the method includes pressing the dies against the test piece to form a plurality of openings therein.

The template 210 generally matches the shape and size of the platform 114 of the test device 100 and includes an open window 212 that is wider than the width of the adhesive tape to be tested and longer than the length of opening 116 in the platform. The window 212 is used to trace a testing area 214 onto the test piece 201. The testing area 214 aides the user in proper placement of the adhesive tape onto the test piece 201 as will be explained below.

Accordingly, once the test sample 104 is complete, the slit 206 (or plurality of openings) is positionable on the testing device 100 with the slit 106 (or plurality of openings) generally aligned and matching the location of the opening 116 (or plurality of openings 156, FIG. 8) in the platform 114. In another embodiment, instead of a slit 206, the test substrate may have an opening suitable for matching the opening in the platform, for example a series of holes arranged within the test area in a line or other patterned or random arrangements.

Figure 7:
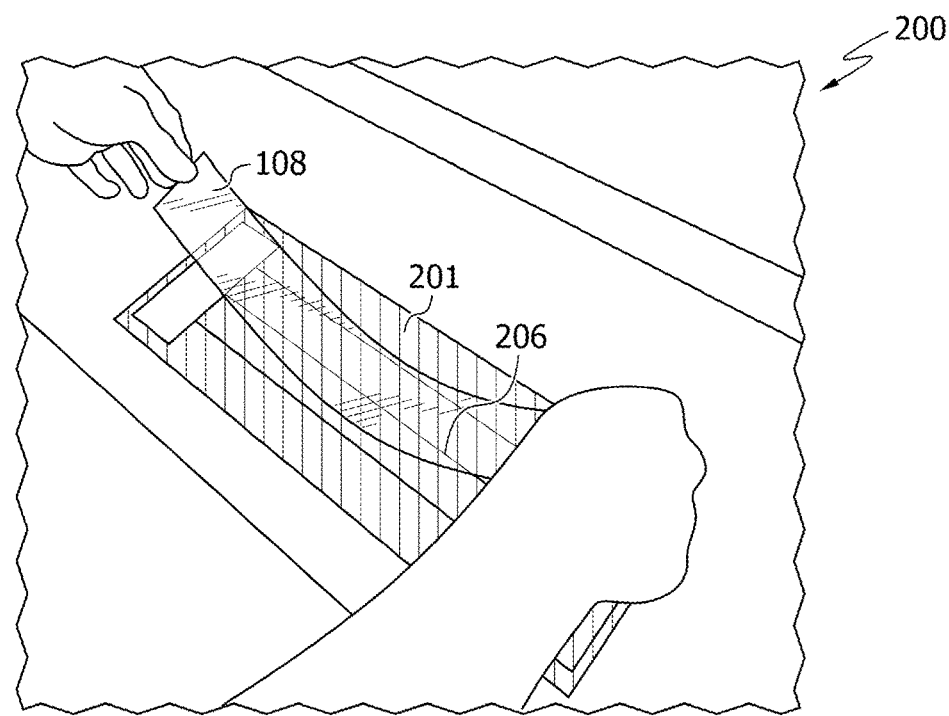

The test piece 201 is now ready to receive a strip of adhesive tape 108 adhered to the testing area 214. As seen in FIG. 7 a user adheres a strip of adhesive tape 108 to the test piece 201 by positioning the adhesive tape 108 carefully within the testing area 214. The tape 108 is applied in a single ply to cover slit 206, ensuring that the test substrate 104 material remains flat and unfolded/unbent. If the adhesive tape 108 incorporates a pressure-sensitive adhesive, uniform pressure should be applied to the tape 108 to ensure a complete and uniform bond between the tape 108 and the test substrate 104. A length of the strip of adhesive tape 108 may be generally longer than a length of the slit 206 such that the strip of adhesive tape 108 completely covers the slit 206. In one embodiment, the adhered tape 108 is sized such that it extends at least about one inch beyond both ends of the slit 206. For uniformity in testing the seal strength, the process should include a standard for application of pressure to adhere the adhesive tape 108 to the test substrate 104, such as, but not limited to, PSTC 101 guidelines. By following the PSTC 101 guidelines, the process includes rolling a one pound roller the length of the adhesive tape. Additionally other devices may be employed to adhere the tape to the test piece, for example, squeegees, widgets, spreaders, and the like. In one embodiment, the squeegee is held at a 45 degree angle with a one pound weight affixed thereto and is moved along the length of the adhesive tape one or more times. After the adhesive tape 108 is applied to test piece 201 having slit 206, the combination is referred to as the test sample 102.

The operation of the testing device 100 to test the seal strength of a test sample 102 includes, with the frame 120 removed from the platform 114, placing the test sample 102 on the platform 114 with the slit 206 generally aligned with the opening 116 in the platform 114. The test sample 102 is positioned on the platform with the tape side facing upward away from the platform 114, as shown in FIG. 2. The frame 120 is lowered to sandwich the test sample 102 between the frame 120 and the platform 114 and the fasteners 132 are moved into their closed positions to hold the frame 120 in place, thereby securing the testing device 100 in the closed position. A fluid-tight or air-tight seal 144, as appropriate in view of the fluid to be used for the testing procedure, is thereby established between the test sample 102 and the platform 114. The strength of this fluid-tight/air-tight seal 144 should be greater than the anticipated strength of the test seal 150, such that upon the application of pressure to the system, the test seal 150 will fail before the seal 144.

With the test sample 102 positioned and secured in the testing device 100, testing of the test seal 150 can commence. Fluid is allowed to flow into the chamber 112 via the inlet 118 typically in a controlled manner. In one embodiment, a pump may be used to supply a flow of air and the flow rate may be controlled by the regulator 122 and monitored by the airflow meter 124. In another embodiment, a fluid other than air may be used, such as nitrogen gas, carbon dioxide, or water.

The fluid-tight/air-tight seal 144 between the test sample 102 and the platform 114 prevents the flow of fluid beyond the space defined and bounded by the platform 114 and the bottom surface of the test sample 102. As fluid flows into the system through the inlet 118 of the chamber 112, pressure builds up within the chamber 112, which can be monitored, for example with the pressure gauge 126. The pressure from the amount of fluid within chamber 112 applies a force to the underside of the test sample 102, thereby stressing the test seal 150 along the opening 106 of the test substrate 104. By design, the test seal 150 is weaker than the fluid-tight/air-tight seal 144 so that adhesive failures between the adhesive tape 108 and the test substrate 104 can be observed and quantified.

During the testing process, the test sample 102 is monitored for the occurrence of failure points along the test seal 150 and/or a massive failure of the test seal 150. A "failure point" is defined as: 1) a bubble of air (or other applicable fluid) between the test substrate 104 and the length of adhesive tape 108, or 2) a leak in the test seal 150 permitting outflow of the air (or other applicable fluid) from between the test substrate 104 and the length of adhesive tape 108. A "massive failure" is defined as occurring when: 1) there is a significant drop in pressure within the chamber 112, or 2) an increase in flow of fluid through the inlet 118 does not increase the pressure within the chamber 112. The test sample 102 may be monitored for failure points and/or massive failure at the completion of a predefined duration of airflow establishing a particular pressure, during a portion thereof, or continuously through some or all of the testing process.

Referring back to FIGS. 2 and 3, failure points may be difficult to detect with the naked eye. Thus, a failure detecting agent 146 may be applied to the test sample 102, for example with an eye dropper (ED), prior to application of a fluid into chamber 112, to make failure points easier to see or otherwise detect during the testing process. The failure detecting agent 146 may be a visual aid, such as a liquid incorporating a dye (for example, malachite green), applied to the test substrate 104 along the outer perimeter 148 of the test seal 150. The failure detecting agent 146 may be a detergent or detergent solution or further include a detergent, such as a standard dish detergent that will readily form bubbles if subjected to a stream of air from a failure point in the form of a test seal 150 leak. In one embodiment, the failure detecting agent 146 is 89% water, 1% dye, and 10% dish detergent, by volume.

In another embodiment, failure detection may be accomplished by laying a piece of material or a plurality of pieces of material over the outer perimeter 148 of the test seal 150 such that a leak would move, rustle, or scatter the piece or pieces of material. To prevent the piece or pieces of material from being falsely moved by ambient conditions, the testing device 100, as seen in FIG. 3, may optionally include a cap 158 sealingly seated against an outer surface of the frame 120 to define a second chamber 160. The seal may be enhanced by the inclusion of a sealing member 159 therebetween.

Figure 9:
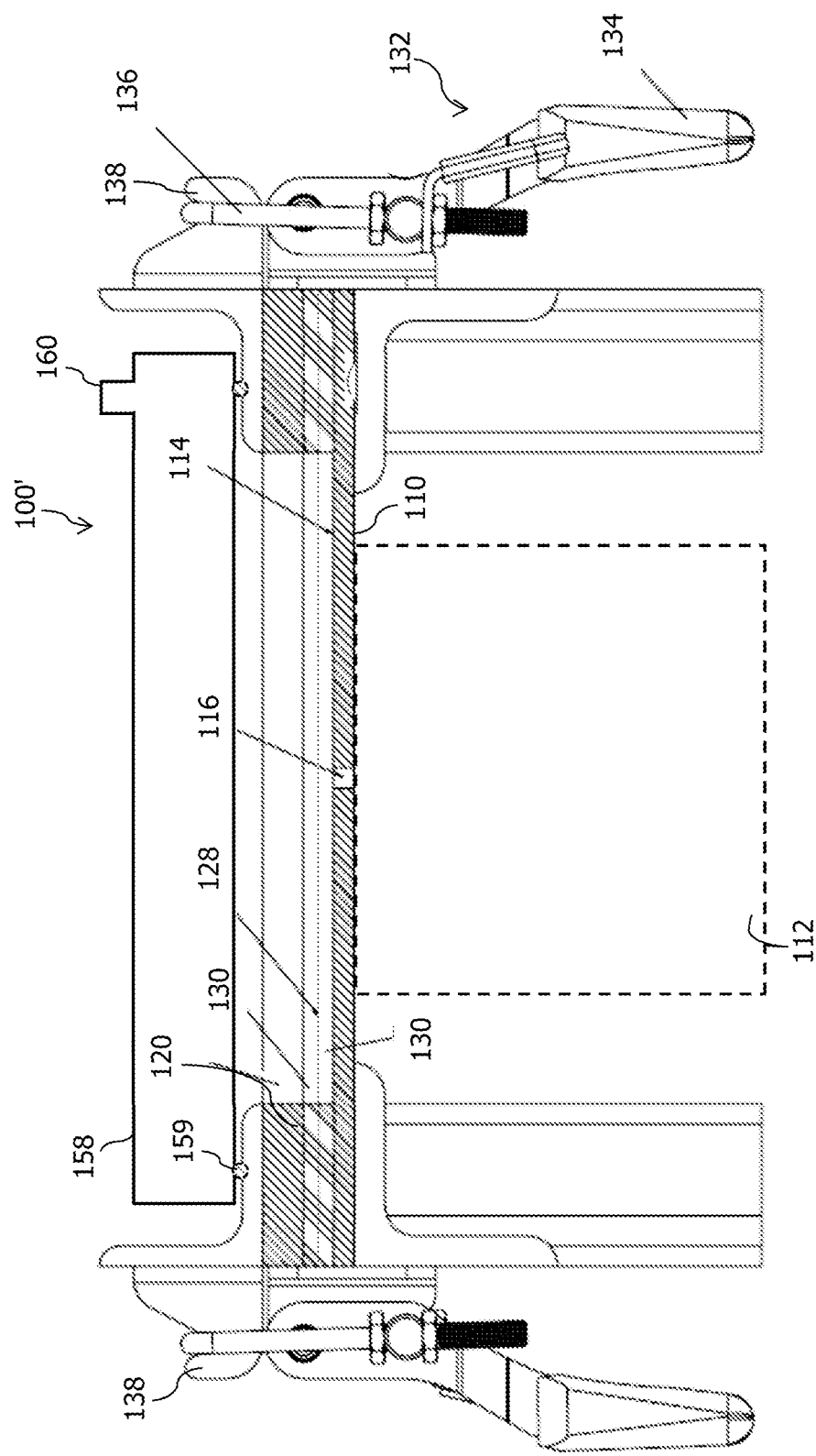
FIG. 9 is a cross-sectional view transverse to the longitudinal axis of another embodiment of the testing device disclosed herein.

In the embodiments described above fluid was introduced into chamber 112 of FIG. 3 to apply pressure to the test seal 150, but the testing device is not limited thereto. In another embodiment, such as in FIG. 9, the testing device 101' operates by the removal of fluid from an upper chamber 158 through a port 160 in fluid communication therewith, which creates a lower pressure inside chamber 158 and enables a higher ambient pressure to act upon the test seal by application of pressure to the test piece through the opening 116 (or a plurality of openings) in the platform 114. Here, chamber 158 is present above the platform 114, and more specifically is mounted to the surface of the frame 120 opposite the surface which is seated on the platform 114. Optionally, the lower chamber 112 may also be present and introduces additional means to control the pressures applied to the test seal rather than ambient pressures being applied opposite chamber 158. A benefit to the presence of both the upper chamber 158 and the lower chamber 112 is the ability to add a pressure sensor to one or more of the chambers 158, 112 to detect any changes in pressure that would be indicative of a failure of the test seal.

Using these basic principles, the testing device 100 may be incorporated into any of a variety of testing protocols to test the strength of a given substrate 104-adhesive tape 108 pairing and to comparatively evaluate seal strengths of various pairings under various types of stress. In one embodiment, the air inflow rate into the chamber 112 may be continuously increased until massive failure of the test seal 150 is detected, and the pressure required to achieve the massive failure is monitored and recorded. In another embodiment, the testing device 100 may be maintained at a predefined target pressure indefinitely (or up to a predefined maximum period of time on a pass/fail basis), and the length of time elapsed before massive failure and/or a specified number of failure points is monitored and recorded.

In another embodiment, a series of incrementally increasing target pressures are predefined, and the inflow of air into the chamber 112 is periodically increased from one target pressure to the next target pressure, where at each target pressure, the pressure is held constant for a set interval of time and the number of failure points at that pressure is monitored and recorded. This process is then repeated until there is a massive failure. Suitable predefined target pressures include, for example, about 0.10, 0.25, 0.50, 0.75, 1.0, 1.5, 2.0, 3.0, and 4.0 psi. Suitable time intervals for maintaining a given pressure include, for example about thirty seconds, about one minute, or about two minutes, or some other predetermined time limit.

Through the use of the disclosed device and method, the effectiveness of a particular sheathing tape-substrate combination can be quantitatively and qualitatively evaluated prior to a commercial application to predict the suitability of a given tape-substrate combination for a particular purpose, thereby decreasing the likelihood of sheathing tape failure and the problems attributable to such failure.

The embodiments of this invention shown in the drawings and described above are exemplary of numerous embodiments that may be made within the scope of the appended claims. It is contemplated that numerous other configurations of the testing device and methods for testing the seal strength of tapes may be created by taking advantage of the disclosed approach. However, the scope of the patent issuing herefrom will be limited only by the scope of the appended claims.

What is claimed is:

1. A testing device for testing adhesion seal strength of an adhesive tape to a substrate comprising:
    a body defining a chamber having a first port in fluid communication with the chamber;
    a platform sealingly attached to the chamber and having an elongate opening or a plurality of openings extending through the platform from a chamber facing surface to an opposing test-sample facing surface, wherein the elongate opening or the plurality of openings define a second port of the chamber; and
    a frame removably mounted to the platform, wherein the frame defines a first perimeter surrounding the second port and, when the frame is mounted to the platform in a test position, the frame is configured to secure a test substrate thereunder against the platform with a fluid-tight seal.

2. The testing device of claim 1, further comprising a regulator coupled to the first port for introduction of a gas into the chamber.

3. The testing device of claim 1, further comprising one or more fasteners removably mounting the frame to the platform.

4. The testing device of claim 1, further comprising a pressure gauge in fluid communication with the chamber.

5. The testing device of claim 1, further comprising a gas-flow meter in fluid communication with the chamber.

6. The testing device of claim 1, wherein the test-sample facing surface of the platform further comprises a seal positioned generally along a second perimeter of the platform to create the fluid-tight seal with the test substrate when the frame is in the test position.

7. The testing device of claim 1, wherein the body defining the chamber is below the platform opposite the frame, and the first port acts as an inlet for fluid.

8. The testing device of claim 1, wherein the body defining the chamber is mounted to an upper surface of the frame opposite a lower surface thereof, which is seated on the platform, and the first port acts as an outlet for fluid.

9. The testing device of claim 7, further comprising a second body sealingly mounted to an upper surface of the frame opposite a lower surface thereof, which is seated on the platform thereby defining an upper chamber; wherein the upper chamber includes a third port.

10. The testing device of claim 9, wherein the chamber and/or the upper chamber includes a pressure sensor.

11. A method for testing the adhesion seal strength of tape to a substrate comprising:
    providing a tape testing device, the device comprising:
        a body defining a chamber having a first port in fluid communication with the chamber;

a platform sealingly attached to the chamber and having an elongate opening or a plurality of openings extending through the platform from a chamber facing surface to an opposing test-sample facing surface, wherein the elongate opening or the plurality of openings define a second port of the chamber; and a frame removably mounted to the platform, wherein the frame defines a first perimeter surrounding the second port and, when the frame is mounted to the platform in a test position, the frame is configured to secure a test substrate thereunder against the platform with a fluid-tight seal;

providing a test substrate having an opening therethrough that generally matches the elongate opening or plurality of openings in the platform and a length of adhesive tape adhered thereto in a position that covers the elongate opening or plurality of openings therein to define a test seal;

securing the test substrate between the frame and the platform of the tape testing device with the length of adhesive tape fully visible inside of the first perimeter;

allowing a fluid to flow into or out of the chamber of the testing device using the first port thereof; and monitoring the test seal.

12. The method of claim 11, further comprising applying a failure detecting agent to the test substrate along an edge of the length of adhesive tape, wherein the failure detecting agent is a liquid solution comprising a dye and/or a detergent.

13. The method of claim 11, further comprising applying a failure detecting agent to the test substrate along an edge of the length of adhesive tape, wherein the failure detecting agent comprises a piece of material or a plurality of pieces of material that moves, rustles, or scatters as a result of a leak along the length of the adhesive tape.

14. The method of claim 11, wherein allowing a fluid to flow into the chamber includes selecting a target pressure and adding fluid until the target pressure is achieved.

15. The method of claim 11, wherein allowing a fluid to flow into the chamber includes selecting a first target pressure and a second target pressure, and adding fluid until the first target pressure is achieved, and thereafter incrementally increasing a flow of fluid into the chamber until the second target pressure is achieved.

16. The method of claim 15, wherein allowing a fluid to flow into the chamber includes gradually, continually increasing the flow of fluid into the chamber until a failure of the test seal occurs and recording a pressure value.

17. The method of claim 11, wherein monitoring the test seal includes visual observation by a user of one or more failure points detectable as a bubble between the test substrate and the length of adhesive tape or a leak of fluid from the chamber.

18. The method of claim 11, wherein the test substrate is house wrap and the adhesive tape is sheathing tape.

19. The method of claim 11, further comprising maintaining, at the target pressure, a constant flow of fluid for a selected interval of time.

20. The testing device of claim 1, wherein the first perimeter defined by the frame has a window with a first width that is greater than a second width of a strip of adhesive tape to be adhered to the test substrate.

* * * * *